United States Patent
Lee

(10) Patent No.: US 10,155,034 B2
(45) Date of Patent: *Dec. 18, 2018

(54) SOFT GEL DELIVERY SYSTEM FOR TREATING POULTRY

(71) Applicant: CEVA ANIMAL HEALTH INC., Guelph (CA)

(72) Inventor: Eng-Hong Lee, Guelph (CA)

(73) Assignee: CEVA ANIMAL HEALTH INC., Guelph (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,609

(22) Filed: Nov. 15, 2016

(65) Prior Publication Data

US 2017/0106069 A1    Apr. 20, 2017

Related U.S. Application Data

(60) Division of application No. 14/324,398, filed on Jul. 7, 2014, which is a continuation of application No.
(Continued)

(30) Foreign Application Priority Data

Apr. 15, 2004    (CA) .................................... 2464522

(51) Int. Cl.
*A61K 39/012*    (2006.01)
*A01K 45/00*    (2006.01)
(Continued)

(52) U.S. Cl.
CPC ............ *A61K 39/012* (2013.01); *A01K 39/01* (2013.01); *A01K 45/00* (2013.01); *A01K 45/002* (2013.01);
(Continued)

(58) Field of Classification Search
CPC ...... A01K 39/01; A01K 39/02; A01K 39/012; A61D 1/025
(Continued)

(56) References Cited

U.S. PATENT DOCUMENTS 1,798,769 A    3/1931  Ward
2,034,968 A    3/1936  Bartlett
(Continued)

FOREIGN PATENT DOCUMENTS

CA    1 204 057    5/1986
CN    87 215 466   6/1988
(Continued)

OTHER PUBLICATIONS

Dasgupta T. et al., A gel delivery system for coccidiosis vaccine: uniformity of distribution of oocysts, Can Vet J., Aug. 2000, 41(8):613-6.
(Continued)

*Primary Examiner* — David J Parsley
*Assistant Examiner* — Danielle A Clerkley
(74) *Attorney, Agent, or Firm* — Oblon, McClelland, Maier & Neustadt, L.L.P.

(57) ABSTRACT

The present invention is directed to a method of treating poultry hatchlings in a hatchling tray. The method comprises of providing a soft gel form capable of being dispensed through a spray nozzle, providing a spray dispensing apparatus, the apparatus being capable of delivering a predetermined volume of the gel as a plurality of small beadlets through a plurality of nozzles, placing the hatchling tray containing the hatchlings beneath the nozzles of the dispensing apparatus, dispensing the predetermined volume of the soft gel containing the therapeutic agent as small beadlets into the hatchling tray and allowing the hatchlings to consume the beadlets. The present invention is also directed
(Continued)

to a dispensing apparatus for dispensing a therapeutic agent in a soft gel into a hatchling tray of poultry hatchlings.

24 Claims, 2 Drawing Sheets

Related U.S. Application Data

11/793,047, filed as application No. PCT/CA2005/000565 on Apr. 14, 2005, now Pat. No. 8,794,185.

(51) Int. Cl.

| | |
|---|---|
| A61D 1/02 | (2006.01) |
| A61D 7/00 | (2006.01) |
| A01K 39/01 | (2006.01) |
| A61K 9/06 | (2006.01) |
| A61K 39/002 | (2006.01) |
| A61K 45/06 | (2006.01) |
| A61K 47/36 | (2006.01) |
| A61K 9/00 | (2006.01) |
| A61K 39/00 | (2006.01) |

(52) U.S. Cl.
CPC ............ *A01K 45/007* (2013.01); *A61D 1/025* (2013.01); *A61D 7/00* (2013.01); *A61K 9/0053* (2013.01); *A61K 9/0095* (2013.01); *A61K 9/06* (2013.01); *A61K 39/002* (2013.01); *A61K 45/06* (2013.01); *A61K 47/36* (2013.01); *A61K 2039/52* (2013.01); *A61K 2039/54* (2013.01); *A61K 2039/542* (2013.01); *A61K 2039/552* (2013.01); *A61K 2039/70* (2013.01)

(58) Field of Classification Search
USPC ............... 119/51.01, 72, 725, 602–605, 72.5
See application file for complete search history.

(56) References Cited

U.S. PATENT DOCUMENTS

| | | |
|---|---|---|
| 2,775,227 A | 12/1956 | Henry |
| 3,242,008 A | 3/1966 | Kurtz |
| 3,930,756 A | 1/1976 | Bruggeman |
| 4,172,113 A | 10/1979 | Featherstone |
| 4,316,464 A | 2/1982 | Peterson |
| 5,006,341 A | 4/1991 | Davis et al. |
| 5,158,761 A | 10/1992 | Kamishita |
| 5,404,922 A | 4/1995 | Sliter |
| 5,865,143 A | 2/1999 | Moore, Jr. |
| 6,110,455 A | 8/2000 | Hargis |
| 6,306,385 B1 | 10/2001 | Lee |
| 6,435,136 B1 | 8/2002 | Segura Munoz |
| 6,779,489 B2 | 8/2004 | Greeson |
| 6,908,620 B2 | 6/2005 | McDougald et al. |
| 6,910,446 B2 | 6/2005 | Johnston, Jr. |
| 7,258,079 B2 | 8/2007 | Foster et al. |
| 2002/0104485 A1 | 8/2002 | Lewis et al. |
| 2002/0104489 A1* | 8/2002 | Storer ................... A01K 45/00 119/650 |
| 2003/0198125 A1 | 10/2003 | Linsen |
| 2004/0170648 A1 | 9/2004 | Francon |
| 2006/0051365 A1* | 3/2006 | Gorenflot ............. A61K 39/012 424/191.1 |

FOREIGN PATENT DOCUMENTS

| | | |
|---|---|---|
| CN | 2 103 252 | 5/1992 |
| EP | 0 134 703 | 3/1985 |
| EP | 0134703 | 3/1985 |
| RU | 2 126 267 | 2/1999 |
| WO | 85/00752 | 2/1985 |
| WO | WO96/25951 | 8/1996 |
| WO | WO04/043612 | 5/2004 |

OTHER PUBLICATIONS

Office Action for U.S. Appl. No. 13/067,121 dated Aug. 25, 2011.
Office Action for U.S. Appl. No. 13/067,121 dated Dec. 15, 2011.
English version of the Written Opinion dated Jun. 20, 2017 in Brazilian Patent Application No. PI0509931-5.
European Search Reported dated Sep. 21, 2018 in Application No. 18175663.6-1109. (9 pages).

* cited by examiner

SOFT GEL DELIVERY SYSTEM FOR TREATING POULTRY

This application is a divisional of U.S. application Ser. No. 14/324,398, filed Jul. 7, 2014, which is a continuation of U.S. application Ser. No. 11/793,047, filed Jun. 15, 2007, now U.S. Pat. No. 8,794,185, the entire contents of which are incorporated herein by reference. U.S. application Ser. No. 11/793,047, now U.S. Pat. No. 8,794,185, is a National Stage of PCT/CA2005/000565, filed Apr. 14, 2005, and claims the benefit of priority under 35 U.S.C. § 119 of Canadian Application No. 2464522, filed Apr. 15, 2004.

FIELD OF THE INVENTION

The present invention relates to a soft gel delivery system for treating poultry in the hatchery. In particular, the present invention relates to a delivery system for use in a hatchery for delivery of a therapeutic agent to poultry hatchlings.

BACKGROUND OF THE INVENTION

There are many circumstances where poultry hatchlings must be treated when they first emerge. Such treatment can include administration of therapeutic agents or it may simply involve maintaining the hydration of the hatchlings during holding and transport. There are many therapeutic agent which are used in the raising of poultry: vaccines, competitive exclusion products, vitamins, minerals, medicaments and many others. A number of such therapeutic agents must be protected from environmental effects while being delivered to the hatchlings.

In particular, poultry hatchlings, within the first few days of life, are required to be immunized against various diseases and the type of vaccine used for each disease dictates its method of administration. Vaccines are usually administered in the hatchery by injection at the time of sorting of the hatchlings from the hatching incubator into holding or transporting trays. Live vaccines may be administered once the hatchlings are established in their brooding areas in the form of aqueous suspensions, either sprayed on feed or added to the drinking water.

One example of a live vaccine is that used to immunize poultry against coccidiosis caused by protozoa of the genus *Eimeria*. Coccidiosis is a very common disease of poultry and there are several species of *Eimeria* which are known to cause such disease. The symptoms and severity of the disease are dependent upon the species of *Eimeria* with which the bird is infected with *E. tenella, E. acervulina* and *E. maxima* being three of the most prevalent species in commercial chickens. At the present time, the protection of poultry against coccidiosis involves two possible methods—use of anticoccidials as feed additives or immunization using a coccidiosis vaccine with immunization being increasingly the preferred route. Coccidiosis vaccines are, at present, comprised of an attenuated or unattenuated species of coccidia in a suitable carrier for administration, the coccidia being capable of causing a mild form of the disease and selected to be anticoccidial susceptible.

One common method of immunization against coccidiosis involves the use of on-feed spray administration while the birds are feeding from flats or other containers. A vaccine comprising of oocysts of *Eimeria* species using water as a carrier is sprayed onto the feed to be provided to the hatchlings. The use of on-feed spray administration requires large doses of oocysts. Uniform exposure of the flocks to the vaccine cannot always be achieved.

Vaccine may also be administered through the use of water proportioning systems including automatic fountains and automatic water medicator or proportioners. However, given the particulate nature of coccidiosis vaccines, it is doubtful that the vaccine may actually make it to the distal end of the water line, resulting in uneven exposure to the flock. Additionally, administration of the vaccine through the water proportioning system requires that after administration of the vaccine, the proportioning system be thoroughly cleaned to remove any residual vaccine.

The administration of vaccine in the drinking water requires that the oocysts remain suspended to provide for even exposure to the flock. One solution to this has been proposed by the present applicant in Canadian Patent 1,204,057, which involves suspending the oocysts in a 1.5% carrageenan solution. While this method has numerous advantages, such as reduced levels of oocysts necessary to provide immunization, as well as ease of administration, there is still a drawback in that the provision of open watering systems to hatchlings could result in the liquid being spilled or wetting the hatchlings, which could potentially affect the health of the hatchlings, especially in cold weather and during transportation when hatchlings are vaccinated in the hatchery.

Another method of administering vaccine is through the use of a spray cabinet, which is utilized in the hatchery to spray the hatchlings with a liquid form of the vaccine. A flat or tray of hatchlings usually containing about 100 birds is placed in the spray cabinet and a predetermined dose of liquid vaccine is sprayed directly on the birds. It is expected that as the birds preen they will ingest the vaccine from their feathers. This method suffers some drawbacks in that uniform exposure of all of the hatchlings may not be easily achieved because constant stirring is required to keep oocysts suspended just before spraying. In addition, as the birds are being sprayed with a water-suspended vaccine, then there is a risk that the hatchlings may become too wet, which may affect the health of the birds.

A gel form of a coccidiosis vaccine has been described in PCT application WO 96/25,951, published Aug. 29, 1996. The gel form vaccine of this application is a self-supporting or sliceable vaccine which is formed into a cylinder which is, in turn, sliced to give a proper amount of the vaccine for each tray of the hatchlings. Alternatively the vaccine may be gelled into a suitable watering trough. While this vaccine overcomes the potential problem of wetting of the birds, it does require that the hatchery workers handle the gel to place it in the hatchery tray.

Thus, there remains a need for a simplified means for administration of therapeutic agents in soft gel form to hatchlings in the hatchery, which provides adequate exposure of the flock to the therapeutic agent while reducing potential problem areas.

SUMMARY OF THE INVENTION

The present invention is directed to a method of treating poultry hatchlings in a hatchling tray. The method comprises providing a soft gel suspended in water and capable of being dispensed through a nozzle arrangement; providing a spray dispensing apparatus; the apparatus being capable of delivering a predetermined volume of the gel from a reservoir through a metered pump to a nozzle arrangement, the nozzle arrangement comprising a manifold having a plurality of nozzle openings along its length capable of dispensing the soft gel as a plurality of small beadlets; passing the hatchling tray containing the hatchlings along beneath the nozzles of the manifold; dispensing the predetermined volume of the soft gel as small beadlets into the hatchling tray and allowing the hatchlings to consume the beadlets.

In one aspect, the present invention is also directed to a dispensing apparatus for dispensing a soft gel into a tray of poultry hatchlings. The apparatus comprises a manifold provided with a plurality of nozzle openings spaced along the length of the manifold, the nozzle openings being sized to permit a soft gel to pass therethrough and be dispersed in the form of small beadlets. The manifold is connected to the outlet of a metered pump capable of dispensing a predetermined volume of the soft gel under pressure and the inlet of the pump is connected to a reservoir for containing the soft gel in a flowable form.

In another aspect of the invention, the soft gel contains a therapeutic agent for treating the poultry hatchlings.

In yet another aspect of the invention, the therapeutic agent is a vaccine.

BRIEF DESCRIPTION OF THE DRAWINGS

Preferred embodiments of the present invention are illustrated in the attached drawings in which.

DETAILED DESCRIPTION OF THE PREFERRED EMBODIMENTS

Figure 1:
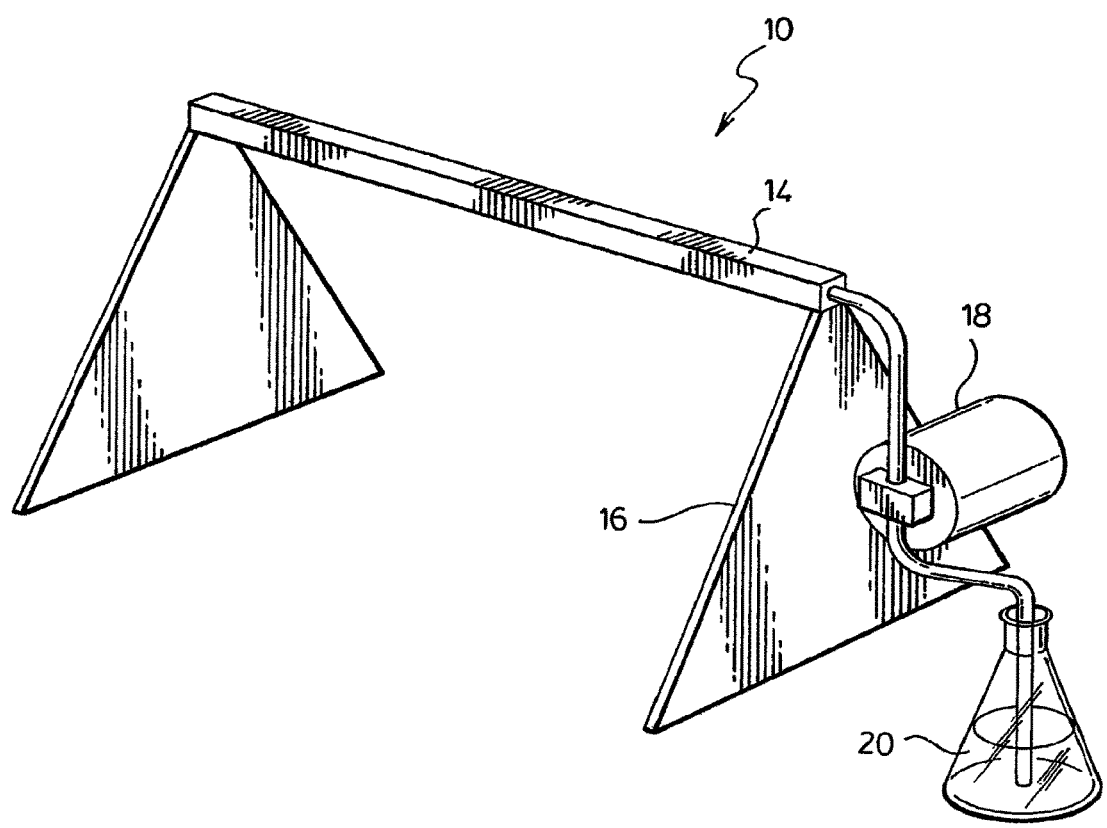
FIG. 1 is a perspective view of a first embodiment of a delivery system of the present invention for use in association with a hatchery conveyor system.
Figure 2:
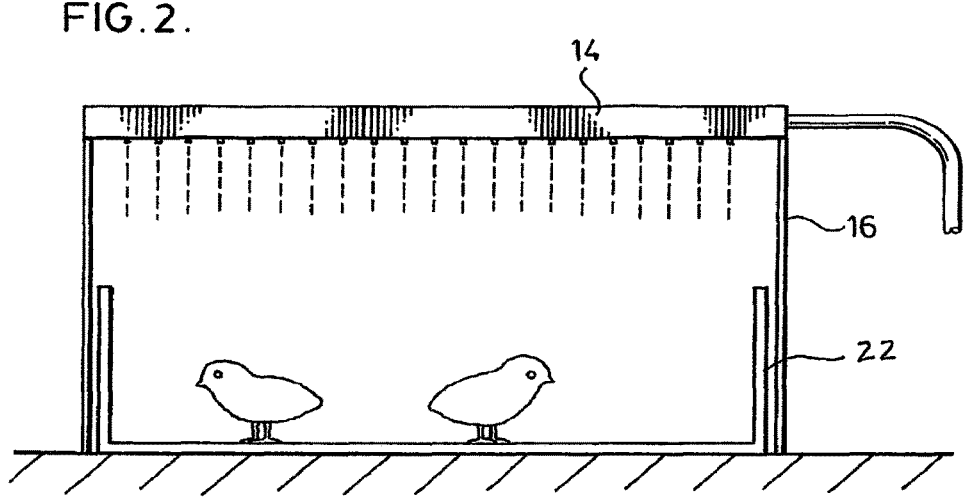
FIG. 2 is front plan view of the delivery system of FIG. 1.
Figure 3:
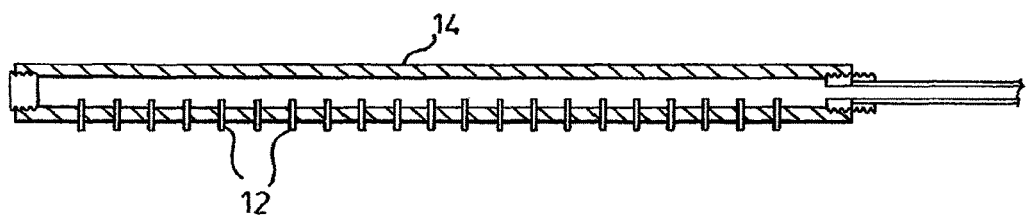
FIG. 3 is a side elevation view in cross section 25 of a manifold of the delivery system of FIG. 1.

The present invention is directed to a method and apparatus for delivering a soft flowable gel to poultry hatchlings for treating the poultry hatchlings. In a preferred embodiment, the soft gel contains a uniform suspension of a therapeutic agent and in a particularly preferred embodiment, the therapeutic agent is a vaccine and the delivery system delivers the vaccine in beadlets of the soft gel to the hatchlings for the purpose of immunizing the poultry hatchlings in the hatchery. The soft flowable gel is capable of being pumped and delivered directly to the poultry hatchlings. The soft flowable gel is dispensed as a plurality of small beadlets which may contain a therapeutic agent and which are easily capable of being ingested by the poultry hatchlings. The gel beadlets retain their moisture content to maintain the viability and/or efficacy of any therapeutic agent contained in the soft gel during the dispensing and consumption of the soft gel. The beadlets help to prevent the moisture from escaping and minimize the potential wetting of the birds.

The soft flowable gel utilizes a suitable setting agent that can form the soft gel at relatively low concentrations to allow the soft gel to contain mostly water. Preferably at least 90% by weight of the gel is water, more preferably at least 95% by weight and most preferably about 98% by weight. The suitable setting agent is preferably a polysaccharide setting agent which sets rapidly to maintain the therapeutic agent in a relatively uniform dispersion throughout the soft flowable gel. More preferably the setting agent is a carrageenan or alginate setting agent which may set either through a change in temperature or through the use of a suitable setting catalyst. Most preferably, the setting agent is a kappa or lambda carrageenan setting agent, which sets through a change in temperature.

The soft flowable gel provides for an easy to handle method of treating poultry hatchlings in the hatchery and is, therefore, suitable for general hatchery workers without any special expertise required. The soft flowable gel is produced utilizing an edible temperature setting polysaccharide gel, preferably a low temperature setting alginate or carrageenan gel, more preferably a lambda or kappa carrageenan gel and most preferably a water soluble lambda-type carrageenan extracted from the red algae *Eucheuma cottonii*.

The soft flowable gel is prepared by dissolving the gel powder in water at a suitable temperature to effect dissolution of the polysaccharide powder. The powder is added to the water at a concentration such that, when mixed with any therapeutic agent and allowed to gel, a soft flowable gel results. Typically, for gels containing therapeutic agents, the dissolved gel powder and therapeutic agent are mixed at a ratio of gel powder to therapeutic agent sufficient to produce the soft flowable gel having the therapeutic agent uniformly suspended therein. For highly soluble agents administered at low doses the ratio may be as high as 1,000:1 (V/V) of dissolved gel powder to therapeutic agent. For large particulate therapeutic agents, such as organisms used for immunization or competitive exclusion products, the ratios will generally be in the range of dissolved gel powder to the therapeutic agent of about 1:1 (V/V) to about 20:1 (V/V). Suitable such soft flowable gels have been found to have a final concentration of the edible polysaccharide in the gel form of between about 0.6 and 1.5 percent, preferably between about 0.6 and 1 percent, more preferably between about 0.8 and 1.0 percent and most preferably about 1.0 percent. Thus preferably, where the ratio of dissolved gel powder to therapeutic agent such as *Eimeria* oocysts suspension is about 1:1 (V/V), a dissolved polysaccharide gel solution of about 1.2 to 3 percent, preferably about 1.2 to 2 percent, more preferably about 1.6 to 2.0 percent, most preferably about 2.0 percent, is mixed with an equal volume of a suspension of oocysts and the mixture allowed to gel.

The soft flowable gel when used as a vaccine, has sufficient levels of the immunizing organisms to provide immunization to the flock. It has been found that for the method of the present invention about 15 to 50 ml of gel for every 100 birds is used, for chickens, preferably about 20 to 30 ml, more preferably about 20 to 25 ml, most preferably about 25 ml of the gel while for turkey poults, preferably about 20 to 40 ml, more preferably 25 to 35 ml, most preferably 35 ml. The concentration of the immunizing organisms in the gel should be such as to provide sufficient organisms in this typical volume to immunize the hatchlings. It has been found that for *Eimeria* between about 50 and 1,000 oocysts per bird provides adequate protection and so it is preferred if the soft gel has between about 200 and 4,000 *Eimeria* oocysts per ml of gel, to provide for proper immunization of the flock. Preferably, the soft gel vaccine contains between about 200 and 400 oocysts per ml of gel, most preferably about 250 oocysts per ml of gel. For a soft gel prepared by mixing the dissolved polysaccharide powder with the oocyst suspension in a ratio of about 1:1 (V/V), one volume of a 1 to 3% polysaccharide gel solution is mixed with an equal volume of oocyst is suspension containing between about 400 and 8,000 oocysts per ml, more preferably one volume of a 1.2 to 2 percent polysaccharide solution with an equal volume of oocyst suspension containing between about 400 and 800 oocysts per ml, most preferably a 2.0 percent solution of polysaccharide solution is mixed with an equal volume of oocyst suspension containing about 500 oocysts per ml. The soft gel vaccine may also be prepared by mixing the dissolved polysaccharide powder with a concentrated oocyst suspension at a higher ratio of dissolved gel powder to oocysts suspension up to about 20:1 (V/V). For example, 2 liters of a 1 to 2% polysaccharide solution may be mixed with 120 ml of an oocyst suspension containing a total of about 1.5 to 3×106 oocysts to prepare the soft gel vaccine.

The use of the edible polysaccharide gels results in a gel which sets rapidly, generally in about 2 minutes or less. This maintains any therapeutic agents such as vaccine organisms in uniform suspension and allows for more uniform exposure of the poultry hatchlings to the therapeutic agents, such as immunizing organisms. Unlike suspension in water, oocysts in the soft gel, after preparation with a mixer will remain suspended without further agitation for up to 24 hours.

The low content of the edible gum in the soft gel means that preferably 95% by weight or more of the gel is water which, when used with or without therapeutic agents, can aid in the hydration of the bird and induce the feeding response. The soft gel has other advantages over liquid suspensions in that the gel will not wet the bird as much and therefore will not affect the health of the chicks, particularly in winter when, if the hatchling becomes wet through exposure to aqueous solution, the exposure may cause death of the hatchling.

The therapeutic agent utilized with the soft flowable gel of the present invention may be one or more of vitamins, minerals, medicaments, vaccines, competitive exclusion products, etc. The soft flowable gel of the present invention is particularly useful for administration of live organisms, such that are used in competition exclusion products or vaccines. Competitive exclusion products are probiotics, for example, such as *Lactobacillus acidophilus*, which are utilized to populate the gut of the poultry and help minimize the potential infection of the poultry with pathogenic organisms, such as *Salmonella, Clostridia*, etc. One example of such a competitive exclusion product is sold by Orion Corp., Finland under the tradename Broilact.

The soft flowable gel is preferably utilized for administration of vaccines, particularly, live vaccines to poultry. Such vaccines may include live *Salmonella* vaccines, Infectious Bronchitis, Infectious Bursal disease, Newcastle disease, Infectious Laryngotracheitis, *Mycoplasma* sp., Pneumovirus and coccidiosis. The soft flowable gel of the present invention is of particular use to the poultry for administration of coccidiosis vaccine containing *Eimeria* sp.

The amount of the therapeutic agent utilized in the soft flowable gel is adjusted to provide for the optimum therapeutic dose to the poultry hatchlings based upon the amount of gel being delivered to the hatchling. It has been found that typically each of the hatchlings will ingest between about 0.15 and 0.5 ml of gel and the concentration of the therapeutic agent is adjusted to provide the optimum therapeutic dose in this volume of gel.

The use of the edible polysaccharide gel which gels rapidly is also suitable for adding nitrogen nutrients and other additives such as vitamins to the soft flowable gel. This is especially useful with heat sensitive nutrients which, if exposed to temperatures over about 50° C., are denatured or inactivated.

The amount of the polysaccharide setting agent is selected to form a soft flowable gel. If too much setting agent is used the gel is not easily flowable and thus is difficult to pump through the delivery system. If too little setting agent is used the gel form may not maintain any therapeutic agent contained in the gel such as immunizing organisms in a relatively uniform suspension. In addition, too little setting agent may also not trap the moisture properly and may allow the water to escape, which can result in reduced viability of the immunizing organisms as well as causing wetting of the birds.

The following examples are utilized to illustrate preferred embodiments of the present invention but are not to be construed as limiting the scope of the invention to the specific examples.

Example 1

From tests conducted to determine the proper amount of the setting agent to be utilized to maintain *Eimeria* oocysts in suspension, it was determined that a gel having a viscosity of at least 23 cps is required to maintain the oocysts in suspension. With carrageenan gel, this translates to about 0.6 percent carrageenan gel. The gel may contain more carrageenan than 0.6 percent, however it has been found that greater than about 1 percent gel does not provide any added advantage in maintaining the oocysts in suspension and may cause difficulties in delivery of the flowable gel. For carrageenan, the preferred range of gel is 0.8 to 1.0 percent with 1.0 percent being the most preferred.

As set out above, for *Eimeria* oocysts which are rather large and dense organisms, a gel having a viscosity of at least 23 cps is required to maintain the oocysts in suspension. If the immunizing organisms in the gel are smaller or lighter, then a lower viscosity gel may be utilized to maintain the organisms in suspension. The proper amount of gel to utilize to maintain the suspension of organisms, while also entrapping the moisture within the gel matrix, may be easily determined in accordance with the example set out above.

A first embodiment of a delivery apparatus of the present invention is illustrated in the figures generally indicated by the numeral 10. The apparatus 10 has a manifold 14 having a plurality of nozzle openings 12 along the length of the manifold 14 to enable spraying of the gel into a hatchling tray 22. The manifold 14 is spaced above the hatchling tray 22 by two supports 16 having a height to space the manifold 14 above the hatchling tray 22 and being spaced apart a distance to straddle the tray 22. The delivery apparatus 10 has a pump means 18 to enable the soft flowable gel to be pumped through tubing and dispensed into the hatchling tray 22 through the nozzles 12 located in the manifold 14. The pump means 18 is preferably a metered diaphragm pump as the motion of the diaphragm vibrates or agitates the fluid flow helping to disrupt the fluid flow and cause the soft gel to be released as a series of discreet droplets. The tubing from the manifold 14 is connected to an outlet of a metered diaphragm pump 18 and the inlet of the diaphragm pump is connected to a container or reservoir 20 containing the soft flowable gel. One such metered diaphragm pump is that used for chlorine dosing such as ProMinent Gamma Solenoid dosing pumps. The use of a diaphragm pump with chemical resistant parts also allows the apparatus to be washed by pumping warm detergent solutions and to be sterilized by pumping chlorine containing solutions through the apparatus. This makes clean up of the apparatus very simple and provides effective disinfection.

The size and spacing of the nozzles of the manifold is selected to produce a pattern of small beadlets of the soft gel. It has been determined that a manifold containing 20 to 35 nozzles spaced 1 to 2 cm apart along the length of the manifold are preferred. Preferably, to allow for delivery of small beadlets of gel, the inner diameter of the nozzles is about 1 mm. It has been found that providing the nozzles as small tubes extending slightly into the manifold, helps in the dispensing of the soft gel as beadlets and reduces the likelihood of the gel dripping from the nozzles when the pump is not operating.

Example 1

The apparatus described above was configured to deliver 25 ml of gel to each hatchling tray containing about 100 birds. Day-old cockerels were divided into two groups, a treatment group and a positive control group. The positive control group had 11 birds, from which one bird was inoculated with one ml of gel, five birds were inoculated with 0.5 ml of gel which was done via gel spray. The remaining five birds were inoculated with 0.5 ml water containing about $2 \times 10^5$ oocysts per ml. The carrageenan gel at 1.0 percent containing approximately $2.5 \times 10^5$ oocysts per ml of gel was made and mixed with 6.7 percent blue dye. The treatment group of 92 birds was used for gel spraying. Postmortem examination of the digestive tract of 46 of the gel treated birds was carried out at 15, 30, and 60 minutes after spraying. The remaining birds were examined 5 and 6 days after spraying and lesions were scored from 0 to 4 with 0 being normal and 4 being the maximal lesions.

Positive evidence of vaccination was observed in two ways—colored blue beaks, tongues and crops by the blue dye in the gel and the appearance of lesions in duodenum five days after vaccination and ceca 6 days after vaccination. In the postmortem examination of 46 of the sprayed birds carried out at 15, 30 and 60 minutes after gel spraying, 45 of the 46 birds or 98 percent picked up the gel as indicated by the blue tongues or blue roofs. Among the birds positive with blue dye, 10 of 16 birds had blue upper esophagi within 30 minutes and 12 of 14 birds had blue crops within 60 minutes.

Postmortem examination carried out after 5 and 6 days of gel spray was done by examining the digestive tract, and particularly the duodenal loop and ceca and scoring the lesions observed. After five days, 17 of 18 birds were positive with an average lesions score of 1.1±0.6 on the duodenal loop and on the ceca. After 6 days 100 percent of the birds were positive with an average lesions score of 0.7±0.3 on the duodenal loop and 0.7±0.4 on the ceca.

It was observed that the gel sprayed on the chicken feathers was picked up within about three minutes after spraying and the gel on the floor of the tray was cleaned up within 30 minutes. The postmortem examination of the upper digestive tract of 46 birds showed that an average of 98 percent of the birds ingested the gel within 60 minutes after spraying, with 22 of 46 birds examined showing blue esophagi or crops after 30 minutes of spraying, which indicated the spray gel was effectively carried deeper into the birds digestive tract. The postmortem examination of the digestive tract of the 42 birds showed that an average of 98 percent of the birds were infected with coccidia. Among the birds examined on day 5, 94 percent were positive with an average lesions score of 1.1±0.6 and after day 6, 100 percent were positive with an average lesions score of 0.7±0.3 on the duodenal loop and 0.7±0.4 on the ceca.

Example 2

Four hundred and twenty commercial strain male broiler chickens (Ross×Ross) were obtained at day 1 of age. Birds were randomized to one of two treatment groups replicated six times. Half of the birds, designated treatment 1, were allocated to one of six litter floor pens, 35 birds per pen. The other half of the birds, designated treatment 2, were vaccinated with gel vaccine using the apparatus of the present invention. All treatment replicates were group weighed before placement. Conventional corn/soybean starter, and grower/finisher diets were prepared. Treatment 1 diets were formulated to contain Maxiban® as the anticoccidial ingredient whereas treatment 2 diets contained no anticoccidial. Birds were offered feed and water ad lib. All birds were individually weighed on days 21, and 49 of the trial. Starter diet was fed to day 21; grower/finisher diet to day 49. Birds were monitored for morbidity and mortality twice daily Table 1 shows body weight, body weight gain, feed intake and feed intake:body weight gain data and percent mortality.

| Treatment | Body Weight (g) | | | Body Weight Gain (g) | | |
|---|---|---|---|---|---|---|
| | Initial | 21 d | 49 d | 0-21 d | 21-49 d | 0-49 d |
| 1. Maxiban® | 42.4 | 806 | 3722 | 764 | 2916 | 3680 |
| 2. Immucox® | 42.4 | 813 | 3739 | 770 | 2926 | 3696 |
| SD | .53 | 31.2 | 106.9 | 31.2 | 84.6 | 107.1 |
| Significance | NS | NS | NS | NS | NS | NS |

| Treatment | Feed Intake (g/bird) | | | Feed Intake: Body Wt. Gain | | | Mortality (%) |
|---|---|---|---|---|---|---|---|
| | 0-21 d | 21-49 | 0-49 d | 0-21 d | 21-49 | 0-49 d | 0-49 d |
| 1. Maxiban® | 998 | 5494 | 6491 | 1.31 | 1.88 | 1.76 | 2.38 |
| 2. Immucox® | 996 | 5610 | 6606 | 1.29 | 1.92 | 1.79 | 2.38 |
| SD | 34.8 | 164.8 | 189.3 | 0.04 | 0.03 | 0.03 | 2.15 |
| Significance | NS | NS | NS | NS | NS | NS | NS |

Body. weight, body weight gain, feed intake, feed utilization and percent mortality were not affected by method of providing coccidial control throughout the trial (P>0.05).

Example 3

To compare the efficacy of gel spray delivery, gel puck delivery, and water diluent delivery of turkey coccidiosis vaccine in a challenge study. Measurements of efficacy include weight gains and lesions scores. Immucox for Turkeys, consisting of *Eimeria meleagrimitis* and *E. adenoeides*, was used for immunization.

Birds were vaccinated at day 1 and housed in single-use cardboard boxes for each treatment, and given feed and water ad libitum. The negative and positive controls were treated similarly and not vaccinated. They were placed in a separate isolation room. To minimize bias all birds were randomly assigned to be in one of the five groups; each bird was tagged and weighed before challenge and again 5 days post-challenge. When birds were 8 days old they were split into two boxes for each treatment group (12-14 birds per box).

Twenty-seven poults were vaccinated at day 1 by the gel spray machine. Approximately 25 mL of the gel spray mixture was pumped onto the poults for their consumption. Twenty-seven poults were vaccinated at day 1 by the gel puck delivery method. Gel puck vaccine was left in the box for 90 min for poults to ingest Twenty-six poults were vaccinated at day 1 by the water delivery method. The vaccine in a mixture of diluent and water was left out for 90 min for poults to drink.

At 15 days of age the poults in the positive control, gel spray, gel puck, and water delivery treatment groups were challenged with a total of 400,000 oocysts/bird. Approximately 55% were *E. meleagrimitis* and 45% were *E. adenoeides*. After challenge the birds were then transferred to clean cardboard boxes at 2 boxes per treatment group. Five days post-challenge, each bird had its weight recorded and was then sacrificed. Lesions of the caeca were scored. Two lesion scores were recorded and averaged for statistical purposes.

One bird died in the negative control group (no treatment, no challenge) on day 13. No other mortality was observed. No lesions were found in the negative control group. The birds in the gel puck delivery group gained the most weight, an average of 66.3 g per bird. Birds in the water delivery, gel spray delivery, and non vaccinated/unchallenged treatment groups gained similar amounts of weight at 59.8 g, 61.4 g, and 62.3 g per bird, respectively. Birds in the unvaccinated/challenged group gained the least amount of weight at 52.3 g.

In this Experiment, a two species turkey coccidiosis vaccine containing *Eimeria meleagrimitis* and *E. adenoeides* was given to poults by three routes: gel spray, gel puck, and water delivery. Both positive and negative control groups were included in the study. Birds were challenged with a high dose of turkey coccidia on day 15. Vaccine delivered by gel puck offered the best protection against a high challenge of turkey coccidia than either water delivery or spray delivery as observed by a better weight gain. However all three routes of delivery provided improved weight gains which were statistically significant (p<0.03) when compared to non-vaccinated challenged controls. When lesion score was the measurement of efficacy, delivery of vaccine by gel spray or water was better than delivery by gel puck. Gel spray offers an alternative to delivery by water or gel puck and is efficacious as judged by weight gains and lesion scores.

The soft flowable gel of the present invention allows for an easy to use system for treating poultry hatchlings. In one embodiment, the treating of the poultry hatchlings involves maintaining hydration of the hatchlings during holding and transport. In this embodiment, the soft gel would comprise the suitable setting agent and water, with at least 90% of the weight of the gel being water, more preferably be at least 95% by weight and most preferably about 98% by weight. When utilizing the soft gel for hydration of the poultry hatchlings, it may be advisable to increase the amount of gel dispensed per hatchling tray up to about 75 ml to allow the hatchlings to ingest the beadlets for a longer period of time. When utilized for hydration, the soft gel in addition to the setting agent and water may also include amounts of vitamins, minerals or other nutrients commonly employed, particularly for delivery in water based systems.

In a preferred embodiment, the soft gel is used for administering therapeutic agents particularly to poultry hatchlings. In particular, the soft flowable gel of the present invention is of most use when administering live organisms, such as found in competitive exclusion products and vaccines to the poultry hatchlings. This is particularly the case where the live organisms are relatively large and are required to be maintained in suspension to allow for each of the hatchlings to be exposed to the optimal immunizing dose of the organism.

The use of the soft flowable gel vaccine also allows for the preparation of multivalent vaccines containing more than one organism commonly utilized for vaccination against respiratory diseases such as Newcastle virus and bronchitis, coccidiosis, and other poultry diseases.

The method and soft gel vaccine of the present invention provides for an easy to use means of immunizing a large number of hatchlings by spraying the vaccine on the hatchlings in the tray. The same method can also be used in the barn, if needed. By incorporating the apparatus into a conveyor system, this is easily accomplished.

Although various preferred embodiments of the present invention have been described herein in detail, it will be appreciated by those skilled in the art that variations may be made thereto without departing from the spirit of the invention or the scope of the appended claims.

I claim:

1. A method of vaccinating poultry hatchlings in a hatchling tray, the method comprising:
   moving the hatchling tray containing poultry hatchlings beneath a plurality of nozzle openings of a dispensing apparatus, the nozzle openings spanning a length or width of the hatchling tray, and
   dispensing a flowable gel containing a therapeutic agent onto the hatchlings in the hatchling tray to form gel beadlets on the hatchlings.

2. The method of claim 1, further comprising forming the flowable gel by mixing a 1.2 to 2.0 percent polysaccharide solution with an oocyst containing suspension.

3. The method of claim 1, wherein the flowable gel is a soft flowable gel.

4. The method of claim 1, wherein the flowable gel comprises at least about 95% water by weight.

5. The method of claim 1, wherein the flowable gel comprises an edible temperature setting polysaccharide gel.

6. The method of claim 1, wherein the flowable gel has a concentration of 400 to 800 oocysts per ml.

7. The method of claim 1, wherein during the dispensing 15 ml to 50 ml of flowable gel are dispensed per 100 hatchlings.

8. The method of claim 1, wherein the dispensing apparatus has between 20 to 35 nozzle openings.

9. The method of claim 1, wherein the therapeutic agent comprises *Eimeria* oocysts.

10. The method of claim 1, wherein the flowable gel has a viscosity of at least 23 cps.

11. The method of claim 1, wherein the gel comprises carrageenan.

12. The method of claim 1, wherein the soft flowable gel maintains the therapeutic agent in relatively uniform suspension.

13. The method of claim 12, wherein the soft flowable gel contains a quantity of setting agent sufficient to trap moisture in the beadlets.

14. The method of claim 1, wherein the soft flowable gel contains probiotics.

15. The method of claim 1, wherein after the dispensing the soft flowable gel each hatchling ingests approximately 0.15 to 0.5 ml of flowable gel.

16. The method of claim 1, wherein the therapeutic agent comprises a coccidiosis vaccine.

17. The method of claim 1, wherein the therapeutic agent comprises a live organism maintained in suspension in the flowable gel.

18. The method of claim 1, wherein the therapeutic agent comprises an organism for vaccination against respiratory disease.

19. The method of claim 1, wherein the dispensing apparatus comprises a plurality of tubes extending from a manifold.

20. The method of claim 1, wherein the gel comprises a setting agent which sets through a change in temperature.

21. The method of claim 1, wherein the gel comprises at least one setting agent such that the gel sets in two minutes or less.

22. The method of claim 1, wherein the gel comprises oocysts that remain in suspension for 24 hours.

23. A method of vaccinating poultry hatchlings in a hatchling tray, the method comprising:

moving the hatchling tray containing poultry hatchlings beneath nozzle openings of a dispensing apparatus, the nozzle openings spanning a length or width of the hatchling tray, and dispensing 15 ml to 50 ml of flowable gel containing a therapeutic agent onto the hatchlings in the hatchling tray to form gel beadlets on the hatchlings, wherein the dispensing apparatus comprises a plurality of tubes extending from a manifold, wherein the gel comprises a setting agent that maintains the therapeutic agent in relatively uniform suspension during dispensing to the hatchlings.

24. A method of vaccinating poultry hatchlings in a hatchling tray, the method comprising:

moving the hatchling tray containing poultry hatchlings beneath nozzle openings of a dispensing apparatus, the nozzle openings approximately spanning a width of the hatchling tray, and dispensing a flowable gel containing a therapeutic agent onto the hatchlings in the hatchling tray to form gel beadlets on the hatchlings, wherein the gel has a sufficient viscosity to maintain the therapeutic agent in suspension for 24 hours.

* * * * *